US012279906B2

(12) United States Patent
Ciofolo-Veit et al.

(10) Patent No.: US 12,279,906 B2
(45) Date of Patent: Apr. 22, 2025

(54) METHODS AND SYSTEMS FOR DETERMINING COMPLEMENTARY ULTRASOUND VIEWS

(71) Applicant: KONINKLIJKE PHILIPS N.V., Eindhoven (NL)

(72) Inventors: Cybèle Ciofolo-Veit, Meudon (FR); Thierry Lefevre, Suresnes (FR); Caroline Denise Francoise Raynaud, Paris (FR); Laurence Rouet, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 651 days.

(21) Appl. No.: 17/282,899

(22) PCT Filed: Sep. 29, 2019

(86) PCT No.: PCT/EP2019/076337
§ 371 (c)(1),
(2) Date: Apr. 5, 2021

(87) PCT Pub. No.: WO2020/074291
PCT Pub. Date: Apr. 16, 2020

(65) Prior Publication Data
US 2021/0345987 A1 Nov. 11, 2021

(30) Foreign Application Priority Data

Oct. 8, 2018 (EP) .................................... 18290115

(51) Int. Cl.
*A61B 8/08* (2006.01)
*A61B 8/00* (2006.01)

(52) U.S. Cl.
CPC ............ *A61B 8/085* (2013.01); *A61B 8/0866* (2013.01); *A61B 8/463* (2013.01); *A61B 8/466* (2013.01); *A61B 8/5223* (2013.01)

(58) Field of Classification Search
CPC ....... A61B 8/085; A61B 8/0866; A61B 8/463; A61B 8/466; A61B 8/5223; A61B 8/145; A61B 8/483; A61B 8/523
See application file for complete search history.

(56) References Cited

U.S. PATENT DOCUMENTS

| 2005/0004465 | A1 | 1/2005 | Abuhamad |
| 2005/0240104 | A1* | 10/2005 | Shim ............... A61B 8/469 600/437 |
| 2007/0249935 | A1 | 10/2007 | Deschinger et al. |
| 2008/0021502 | A1* | 1/2008 | Imielinska ........... G06T 7/0012 607/1 |

(Continued)

FOREIGN PATENT DOCUMENTS

| EP | 2918233 A1 | 9/2015 |
| EP | 2982306 A1 | 2/2016 |

OTHER PUBLICATIONS

Luedders, et al., 2011, Fetal micrognathia: objective assessment and associated anomalies on prenatal sonogram. Prenat. Diagn., 31: 146-151.*

(Continued)

*Primary Examiner* — Bo Joseph Peng

(57) ABSTRACT

The invention provides an ultrasound imaging method for determining complementary views of interest based on an anomalous feature identified in a region of interest of an ultrasound image. The method includes obtaining an ultrasound image of a region of interest of a subject and identifying an anomalous feature within said region. The identified anomalous feature may then be used to determine one or more available complementary ultrasound images of interest of the subject. The one or more available complementary ultrasound images may then be displayed to a user and the complementary ultrasound views to be reviewed may then be selected by the user from the displayed available complementary ultrasound images.

15 Claims, 5 Drawing Sheets

(56) References Cited

U.S. PATENT DOCUMENTS

| | | |
|---|---|---|
| 2015/0011886 A1 | 1/2015 | Radulescu et al. |
| 2015/0257738 A1 | 9/2015 | Kim |
| 2015/0302638 A1 | 10/2015 | Jago et al. |
| 2016/0014344 A1* | 1/2016 | Yoo ..................... H04N 23/80 |
| | | 345/420 |
| 2016/0242740 A1 | 8/2016 | Day |
| 2017/0086790 A1* | 3/2017 | Halmann ............ A61B 8/0858 |
| 2017/0091914 A1* | 3/2017 | Halmann ............ A61B 8/4245 |
| 2017/0367685 A1* | 12/2017 | Zou ..................... G06F 18/22 |

OTHER PUBLICATIONS

International Search Report and Written Opinion for International Application No. PCT/EP2019/076337, filed Sep. 29, 2019, 7 pages.
Baumgartner, et al., "SonoNet: Real-Time Detection and Localisation of Fetal Standard Scan Planes in Freehand Ultrasound", IEEE Transactions in Medical Imaging, 36(11): (2017), pp. 2204-2215.
Yeo, et al., "Fetal Intelligent Navigation Echocardiography (FINE): a novel method for rapid, simple, and automatic examination of the fetal heart", Ultrasound Obstet Gynecol 2013, 42(3):pp. 268-284.
Kroes, et al., "Ultrasound features in trisomy 13 (Patau syndrome) and trisomy 18 (Edwards syndrome) in a consecutive series of 47 cases", Facts Views Vis Obgyn, 2014; 6(4): pp. 245-249.
Palit, et al., "An objective measurement to diagnose micrognathia on prenatal ultrasound", . Clin Exp Obstet Gynecol 35(2):2008, pp. 121-123.
Rotten, et al., "The fetal mandible: a 2D and 3D sonographic approach to the diagnosis of retrognathia and micrognathia", Ultrasound Obstet Gynecol 2002, 19: pp. 122-130.

* cited by examiner

METHODS AND SYSTEMS FOR DETERMINING COMPLEMENTARY ULTRASOUND VIEWS

RELATED APPLICATIONS

This application is the U.S. National Phase application under 35 U.S.C. § 371 of International Application No. PCT/EP2019/076337, filed on Sep. 29, 2019, which claims priority to and the benefit of European Application No. 18290115.7, filed Oct. 8, 2018, which is incorporated by reference in its entirety.

FIELD OF THE INVENTION

This invention relates to the field of ultrasound, and in particular to the field of ultrasound imaging.

BACKGROUND OF THE INVENTION

Ultrasound imaging is used in a wide array of medical imaging applications. When performing ultrasound imaging, it is possible that anomalies may be detected, which may be indicative of an underlying medical condition.

A common application of ultrasound imaging is a fetal screening exam, where the health of a fetus is assessed during a given stage in the pregnancy. During the screening exam, the clinician performs measurements of various specific anatomical structures and compares the values to common measurement tables. When a measurement is not in the normal range, additional examinations and additional measurements are required to confirm that the anomaly is a cause for concern. The additional examinations and measurements typically vary depending on the suspected pathology.

Manually selecting the appropriate additional views to observe the anatomy and manually performing the measurements can be long and difficult, especially if several anatomical regions need to be examined.

There is therefore a need to provide a method for obtaining additional ultrasound views of an imaging region in a more efficient manner without requiring significant additional hardware.

EP 2,918,233 discloses an ultrasound diagnosis apparatus including: a display unit that displays a first screen including at least one marker; a user interface unit for receiving a selection of a predetermined marker; and a display unit to display a first screen including a second ultrasound image having a view of an object that is changed according to the predetermined marker.

SUMMARY OF THE INVENTION

The invention is defined by the claims.

According to examples in accordance with an aspect of the invention, there is provided a computer-implemented ultrasound imaging method, the method comprising:
 obtaining an ultrasound image containing a region of interest of a subject;
 analyzing one or more features of the ultrasound image;
 identifying an anomalous feature of the region of interest based on the analysis of the one of more features;
 automatically determining, based on the identified anomalous feature, one or more available complementary ultrasound images of the subject; and
 displaying the one or more available complementary ultrasound images to a user.

This method provides for the automatic obtaining of ultrasound images relating to an anomalous feature identified in a region of interest, which are complementary to the originally obtained ultrasound image.

For example, an ultrasound image may contain an anomalous feature, which requires further investigation. In order to perform said investigation, multiple complementary views may be required to accurately identify the pathology related to the anomalous feature. The complementary views may be automatically determined without requiring additional input by the user.

The selection of the desired complementary images may be performed by the user, from a list of the one or more available complementary ultrasound images that is automatically selected based on the anomalous feature, or may be performed automatically by finding complementary images among images acquired previously during the exam. The user can then choose and review images among the selected views In an arrangement, the ultrasound image comprises a 3D ultrasound image and wherein the determining of the one or more available complementary ultrasound images comprises obtaining one or more complementary 2D views from the 3D ultrasound image.

In this way, the complementary ultrasound images may be obtained directly from the initially obtained 3D ultrasound image.

In an embodiment, the identifying of the anomalous feature of the region of interest comprises performing organ detection.

By detecting an organ within the ultrasound image, it is possible to identify an anomalous feature within a specific target area. For example, the head of the fetus is an important screening area. By performing skull detection as the organ detection, it is possible to automatically locate the head of the fetus within the ultrasound image.

In an embodiment, the region of interest comprises a part of a fetus.

In this way, the process of fetal screening is simplified and accelerated.

In an arrangement, the identifying of the anomalous feature of the region of interest comprises performing skull and mid-sagittal brain plane detection on the fetus.

The mid-sagittal brain plane, also referred to as the median plane, bisects the fetus in order to provide a profile cross-sectional image. This view may then be used to identify any relevant anomalous features of the fetus, and in particular anomalous features within the head of the fetus.

In a further arrangement, the mid-sagittal brain plane detection comprises:
 performing a multiresolution analysis; and
 performing Hough detection.

In an embodiment, the identifying of the anomalous feature of the region of interest comprises:
 extracting a profile of the fetus; and
 obtaining, based on the profile of the fetus:
  a naso-mental angle; or
  an inferior facial angle.

In this way, the facial angles of the fetus may be used to determine anomalous facial formation if the angles are not within the typical ranges.

In an embodiment, the determining of the one or more available complementary ultrasound images comprises automatically generating a list of possible complementary images based on the identified anomalous feature.

In this way, all of the possible complementary views relevant to the investigation of a given anomalous feature may be considered, thereby providing multiple alternative options when a given view is obstructed or difficult to obtain.

In a further embodiment, the determining of the one or more available complementary ultrasound images further comprises:
comparing the list of possible complementary images to previously acquired ultrasound images of the subject; and
if a previously acquired ultrasound image matches a possible complementary view, selecting the previously acquired ultrasound image as an available complementary ultrasound image.

In this way, previously acquired ultrasound images of the subject may be used to provide the required complimentary views.

In a further arrangement, the obtaining of the one or more available complementary ultrasound images from the 3D ultrasound image comprises:
extracting an anatomical reference structure;
obtaining a complementary 2D view group by extracting one or more 2D planes of interest from the 3D ultrasound image based on the extracted anatomical reference structure.

By extracting an anatomical reference structure as a reference point, it is possible to navigate in the 3D image and extract the relevant 2D views of interest from the 3D image.

For example, the cervical spinal area, or the neck, of the fetus may be used to capture 2D views of the lower head, such as the jaw and mouth, which are of interest for the screening of some pathologies.

In a yet further arrangement, the obtaining of the one or more available complementary ultrasound images from the 3D ultrasound image comprises:
extracting a structural feature from the anatomical reference structure;
determining whether the anatomical reference structure can be tracked in the 3D ultrasound image based on the structural feature;
if the anatomical reference structure can be tracked in the 3D ultrasound image:
extracting 2D planes of interest from the 3D ultrasound image by using the anatomical reference structure as an anatomical landmark.

In this way, a specific structural feature may be used to capture the desired 2D planes of interest from the 3D image. In particular, structural features relating to specific pathologies may be utilized when said pathology is being investigated.

In an embodiment, the anatomical reference structure comprises one or more of:
an organ; and
a skeletal structure.

In this way, it is possible to include views containing information relating to a wide range of different pathologies.

In an embodiment, the organ comprises one or more of: a heart; a kidney; a bladder; a stomach; and the skeletal structure comprises one or more of: a skull; a vertebra; a ribcage; a femur; and a humerus.

According to examples in accordance with an aspect of the invention, there is provided a computer program comprising computer program code means which is adapted, when said computer program is run on a computer, to implement the method described above.

According to examples in accordance with an aspect of the invention, there is provided an ultrasound imaging system, the system comprising:

an ultrasound probe adapted to obtain an ultrasound image containing a region of interest of a subject; and
a processor adapted to:
analyze one or more features of the ultrasound image;
identify an anomalous feature of the region of interest based on the analysis of the one of more features;
automatically determine, based on the identified anomalous feature, one or more available complementary ultrasound images; and
display the one or more available complementary ultrasound images to a user.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
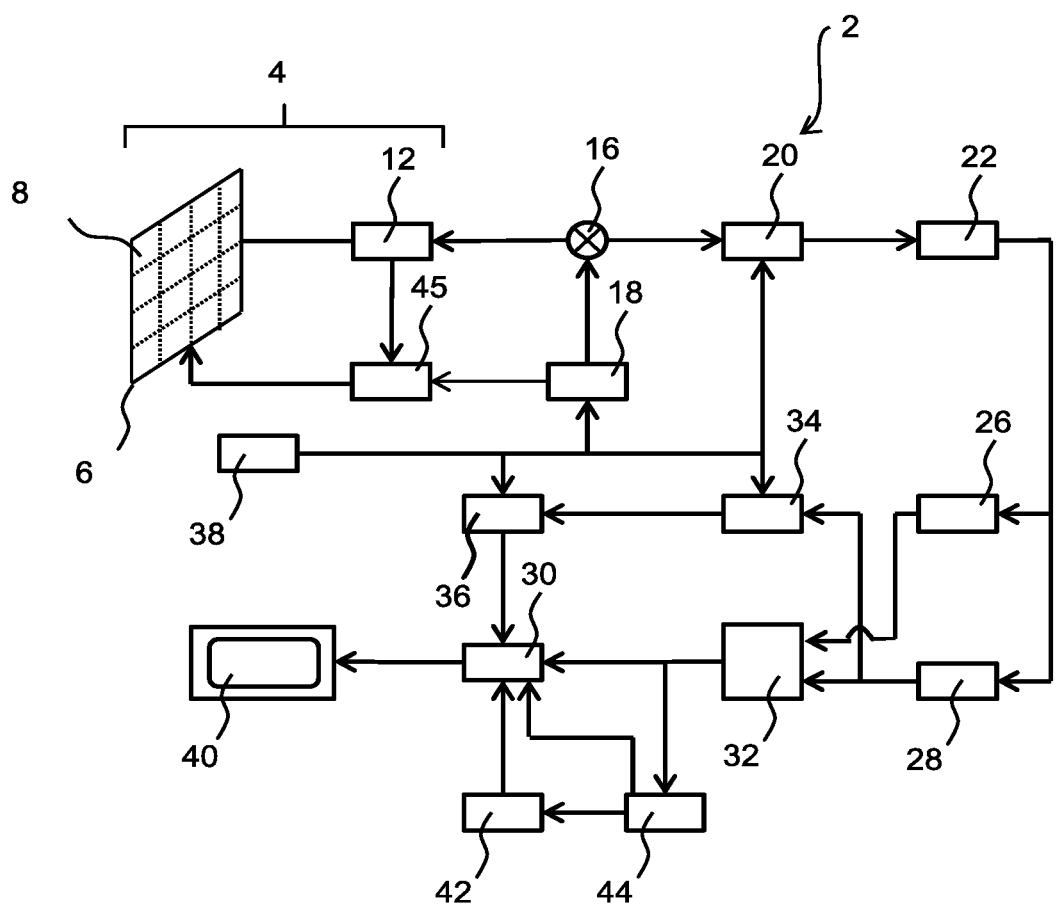
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound imaging method for determining complementary views of interest based on an anomalous feature identified in a region of interest of an ultrasound image. The method includes obtaining an ultrasound image of a region of interest of a subject and identifying an anomalous feature within said region. The identified anomalous feature may then be used to determine one or more available complementary ultrasound images of interest of the subject. The one or more available complementary ultrasound images may then be displayed to a user and the complementary ultrasound views to be reviewed may then be selected by the user from the displayed available complementary ultrasound images.

The general operation of an exemplary ultrasound system will first be described, with reference to FIG. 1, and with emphasis on the image processing function of the system since this invention relates to the processing of the ultrasound images acquired by the system.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the scan signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
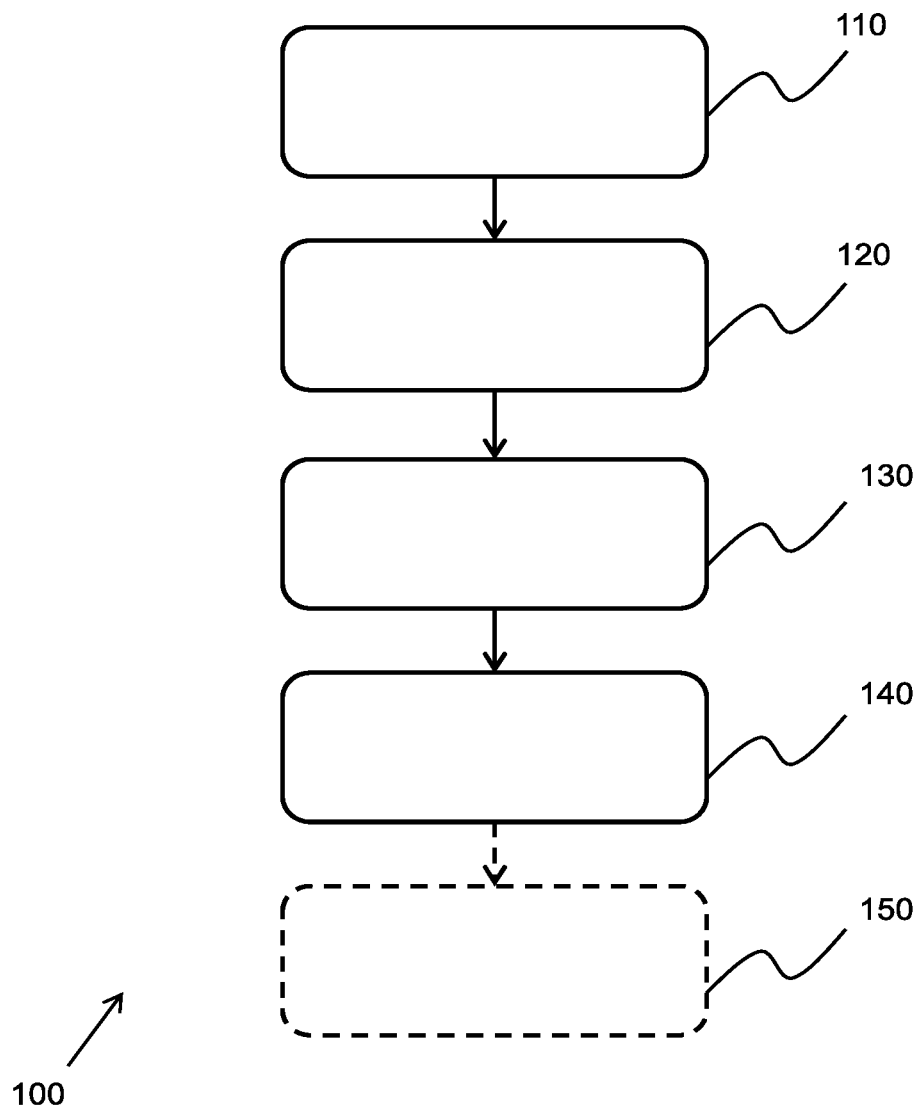
FIG. 2 shows a method of the invention.

FIG. 2 shows a method 100 of the invention.

The method begins in step 110 by obtaining an ultrasound image containing a region of interest of a subject.

The subject may, for example, be a patient undergoing ultrasound screening, in which case the region of interest may be an abdominal area. Further, the region of interest may include at least part of a fetus, in which case the ultrasound imaging method may be used for fetal screening.

Many fetal pathologies are associated with various identifiable features or symptoms. For example, the symptoms of trisomy 13 (occurring in one fetus out of 6500) may include: craniofacial defects; cerebral malformations; genito-urinary tract anomalies; and less frequently, cardiac and finger defects as described in "Ultrasound features in trisomy 13 (Patau syndrome) and trisomy 18 (Edwards syndrome) in a consecutive series of 47 cases.", by Kroes, I., Janssens, S. and Defoort, P. *Facts Views Vis Obgyn.* 2014; 6(4): 245-249.

In step 120, an anomalous feature of the region of interest is identified.

The anomalous feature of the region of interest may be identified automatically using an appropriate automatic image analysis technique, such as feature extraction. For example, automatic feature detection may be used to detection of conditions such as ventriculomegaly in the fetal brain.

Alternatively, the anomalous feature may be identified manually by a user from the obtained ultrasound image. In this case, the user may indicate the identified anomaly to the ultrasound system by selecting an anomalous feature from a list of known anomalous features.

By way of example, the identified feature may be micrognathia (a cranio-facial anomaly corresponding to a small jaw size with respect to the head). According to *Prenatal Diagnosis of Orofacial Malformations*. Tonni G., Sepulveda, W. and Wong, A. E. Springer, 2017: "Micrognathia [ . . . ] is rarely isolated and often associated with other abnormalities, such a hemi-facial macrosomia, Pierre Robin sequence, and Treacher Collins syndrome [ . . . ]. Chromosomal abnormalities have been reported in 66% of fetuses with micrognathia, usually triploidy, trisomy 13, and trisomy 18."

An anomalous feature may be detected either because a measurement obtained from the ultrasound image (obtained either automatically or manually by a user) is not in the normal range (with respect to a common measurement table) or because the user has provided an input for this purpose (for example by using a specific menu with a list of the most frequent anomalies, which may be displayed to the user).

The identifying of the anomalous feature of the region of interest may comprise performing organ detection on the ultrasound image.

For example, in the case of fetal screening, the obtained ultrasound image may contain the head of a fetus, which may be considered as part of the region of interest. In order to facilitate the automatic measurement taking of various typical measurements of the fetal head, the image may undergo organ segmentation, and more specifically skull segmentation.

The segmentation of the skull may be performed, for example, using a dedicated shape transform, which is tailored to detect ellipsoidal shapes in a robust and accurate manner.

In a further example, the identifying of the anomalous feature of the region of interest may comprise performing mid-sagittal brain plane detection on the ultrasound image of a fetal head.

The mid-sagittal plane bisects the head, providing a side profile cross-section of the fetus head. In the example of fetal head screening, the mid-sagittal plane will show a cross-section of the fetus head for use in identifying the anomalous feature.

The mid-sagittal plane may be analyzed in a number of ways. For example, the mid-sagittal plane detection may include performing multiresolution plate structure detection. Multiresolution plate structure detection is a form of multiresolution analysis which uses the eigenvalues of local hessian matrices within the image to detect plate structures.

Further, the mid-sagittal plane detection may include performing Hough detection by way of the Hough transform, which is a feature extraction technique used for recognizing shapes in digital images. For example, the Hough transform may be employed in a method to recognize facial shapes, such as: the nose; the eyes; the skull; and the like.

Further, the Hough transform may be applied to the result of the multiresolution plate structure detection to select the best plane when rotating around an axis of the skull segmentation result.

In addition, the multiresolution plate structure detection and the Hough detection may be incorporated into a single dedicated filter that may be applied to the ultrasound image during the anomalous feature identification process.

The accuracy of the mid-sagittal brain plane may be validated using a deep-learning classifier which checks whether certain expected anatomical structures are present in the image (e.g. corpus callosum, nasal bone) or outside the plane (eyes, lateral ventricles).

The identifying of the anomalous feature may also include extracting a profile of the fetus and obtaining a naso-mental and/or an inferior facial angle, examples of which are discussed below with reference to FIG. 4. The extraction of the fetus profile may be performed automatically with a learning algorithm.

Following the identification of an anomalous feature in step 120, one or more available complementary ultrasound images of interest are determined in step 130. The steps of determining the one or more available complementary ultrasound images is discussed in further detail below, with reference to FIG. 3.

The complementary views may be automatically selected based on the additional views known to be of interest with respect to the detected anomalous feature. In step 140, the user may be presented with a list of complementary views based on the anomalous feature from which they may manually select the desired view. In other words, the one or more available complementary ultrasound images may be displayed to a user. The user may then select the views that they wish to review and the selected view, or views, may then be displayed for review by the user.

In other words, it is possible to automatically determine the available complementary views of interest with respect to the detected anomaly. These views can be chosen from a set of previously stored and annotated views of the same patient in the ultrasound system. The user may then decide which views will be displayed from the list of the automatically selected views.

In step 150, the complementary ultrasound view, or views, selected by the user may be displayed.

Figure 3:
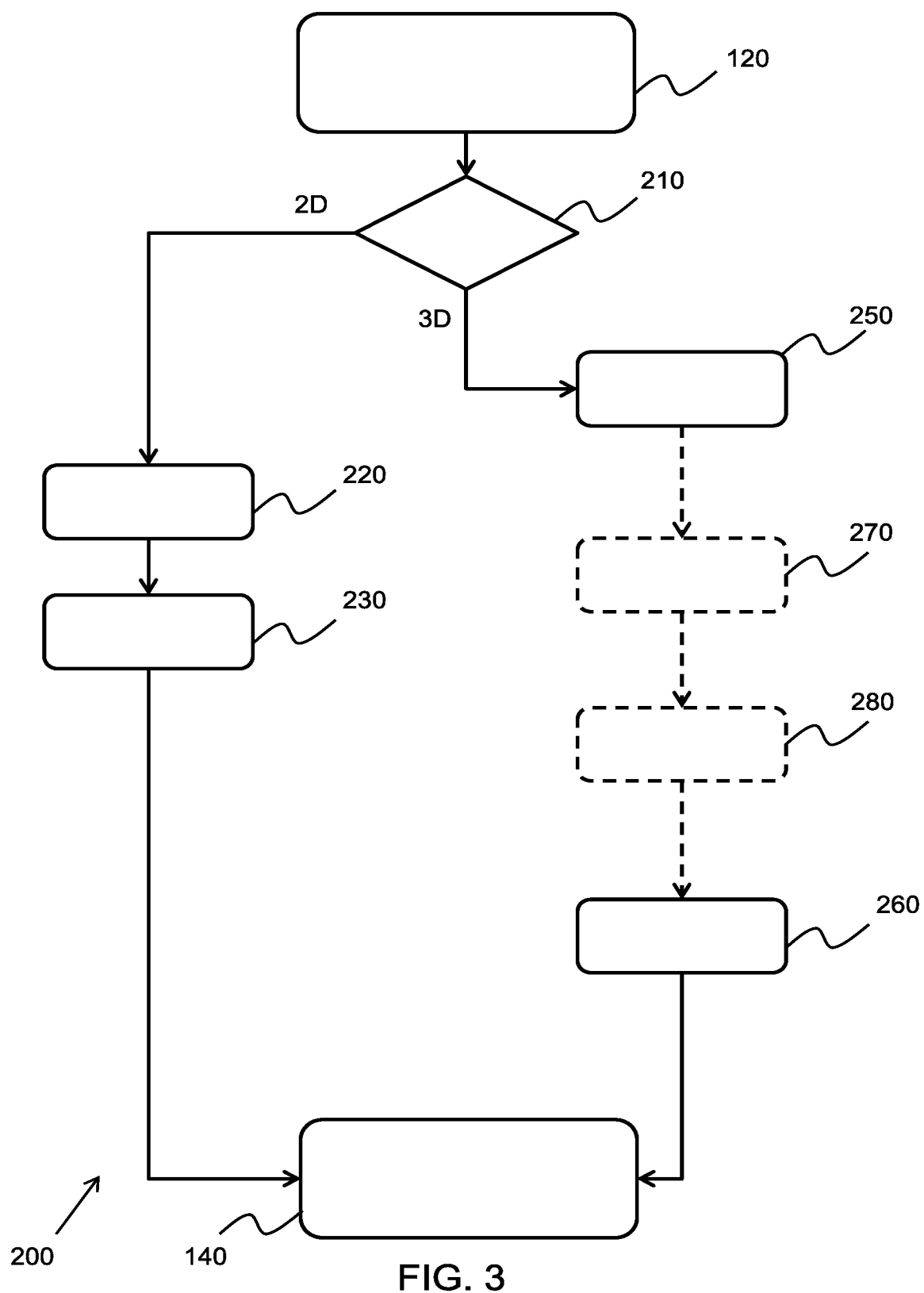
FIG. 3 shows a further method of the invention.

FIG. 3 shows a method 200 for determining the one or more complementary ultrasound images.

The method begins in step 120 where the anomalous feature is identified as described above.

In step 210, it is determined whether a 3D ultrasound image is available.

If a 3D ultrasound image is not available, the method progresses to step 220 where a list of possible complementary images based on the identified anomalous feature is proposed. For example the views may comprise: complementary cerebral views; facial rendering; genito-urinary tract views; cardiac views; and finger rendering.

The listing of these views of interest may be based solely on the knowledge of anomalous features and conditions correlated with the feature detected at step 120, without knowing whether these views are available or not. This list is internal and not displayed to the user.

In step 230 the list of possible complementary images may be compared to previously acquired ultrasound images of the subject. If a previously acquired ultrasound image matches a view of interest acquired in step 220, it is determined that this previously acquired ultrasound image may be used as an available complementary ultrasound image.

If there are no matches between a view of interest and the previously acquired ultrasound images, said view of interest is determined to not be available as a complementary ultrasound image. In this case, it is possible that the user may be directed to select an alternative ultrasound image comprising this view if possible.

Returning to step 210, if a 3D ultrasound image is available the method progresses to step 250.

In the case of a 3D ultrasound image, it is possible to extract the one or more complementary 2D views from the 3D volume by selecting the desired imaging planes within the volume. For the example of fetal screening, the spine of the fetus may be used as a reference structure to extract the complementary 2D views.

The available complementary images are thus the imaging planes which can be generated from the 3D ultrasound image.

In step 250, an anatomical reference structure is extracted.

The anatomical reference structure, which may for example be a cervical spinal area (neck) of a fetus, may be extracted by way of an intensity analysis, for example around the skull of the fetus. In the case that the neck of a fetus is used as the anatomical reference structure, it may be recognized for extraction due to the difference in intensity distributions in the neck area compared to other areas around the skull In step 260, a complementary 2D view group of the one or more complementary 2D views may then be obtained by using the anatomical reference structure as a reference point. In the example of the anatomical area comprising a cervical spinal area, the first complementary view group may contain 2D ultrasound images of the lower head, including the jaw and mouth cavity.

The method may then progress to the displaying of the one or more available complementary ultrasound images, formed of the complementary 2D view group, in step 140 as described above.

The method may also comprise step 270, wherein a structural feature of the anatomical reference structure is extracted. This may be achieved by automatic extraction of the feature using a deep learning algorithm in a stack of slices, or 2D ultrasound images, around the anatomical structure. In the case of vertebrae extraction as the structural feature, the vertebrae may be extracted using 2D ultrasound images in the cervical spinal region, examples of which are discussed below with reference to FIG. 5.

In step 280, it may then be determined whether the anatomical reference structure can be tracked in the 3D ultrasound image based on the structural feature.

By way of example, it may be determined whether the 3D ultrasound image volume contains a greater spinal area larger than the cervical spinal area. In other words, it is tested whether the 3D ultrasound image volume contains the spine extending past the cervical spinal area (neck).

If the 3D ultrasound image does not contain a greater spinal area, the method may simply progress to the displaying of the one or more available complementary ultrasound images in step 140.

However, if it is determined that the 3D ultrasound image contains a greater spinal area, the tangent to the vertebrae stack, or spine tangent, may be estimated and employed as a structural feature. Complementary 2D planes of interest may then be obtained based on the greater spinal area (acting as the anatomical reference structure) and the spine tangent (acting as the structural feature) to form part of the one or more available complementary ultrasound images. Such views may contain slices of the torso and/or abdomen of the fetus, depending on how much of the fetal spine is contained within the 3D ultrasound image. In other words, if the anatomical reference structure can be tracked in the 3D ultrasound image, the 2D planes of interest may be extracted from the 3D ultrasound image by using the anatomical reference structure as an anatomical landmark.

Further, the anatomical reference structure may comprise one or more of: an organ; and a skeletal structure.

For example, the 3D ultrasound image volume may contain a cardiac area.

If the heart is present in the detected plane, the presence of which may be tested with an automated classifier trained on a set of thoracic planes containing or not containing the heart, the plane may be extracted as a cardiac view and stored in the list of available complementary views of interest. In this case, the heart may act as the anatomical structure and a ventricle or atrium of the heart may act as a structural feature to extract the 2D planes of interest in the cardiac area.

Said views of the heart may form a part of the complementary 2D view group of the one or more complementary 2D views.

In a further example, the 3D ultrasound image volume may contain a renal area.

If the kidneys are present in the detected plane, the presence of which may be tested with an automated classifier trained on a set of abdominal planes containing or not containing the kidneys, the plane may be extracted as a genito-urinary view and stored in the list of available complementary views of interest. In this case, a kidney may act as the anatomical structure and a renal artery or renal vein may act as a structural feature to extract the 2D planes of interest in the renal area.

Said views of the kidneys may form a part of the complementary 2D view group of the one or more complementary 2D views.

It should be noted that these cardiac and genito-urinary views are given as examples and similar steps may be applied to other parts of the anatomy, depending on the views of interest of the given anomalous feature and associated pathology. For example, the bladder may also be used as a structure for obtaining complementary view groups. Further, the anatomical structure may comprise: a heart; a kidney; a bladder; a stomach; a skull; a vertebra; a ribcage; a femur; a humerus; or any other suitable organ or skeletal structure.

Each of the images contributing to the 2D complementary view group may form part of the one or more complementary 2D views displayed in step 140.

The above described method may be adapted to other detected anomalous features, wherein the cranio-facial starting point described above is only given as an illustration. For example, if the first detected anomalous is a cardiac one, the same workflow may be used by selecting complementary views of interest stepwise along the spine in both directions (towards the head and towards the pelvis). Similarly, starting from an abdominal anomaly, complementary views of interest can be selected in the direction of the head.

In other words, a complete list of complimentary views may be identified based on an anomalous feature, which corresponds to all known views for assessing a given anomaly. The available complimentary views may then be determined from said list based on the content of the obtained ultrasound image. The available views may then be presented to the user for selection or be automatically selected. Alternatively, if further imaging is required, the user may be directed to obtain one or more of the complimentary views.

Figure 4:
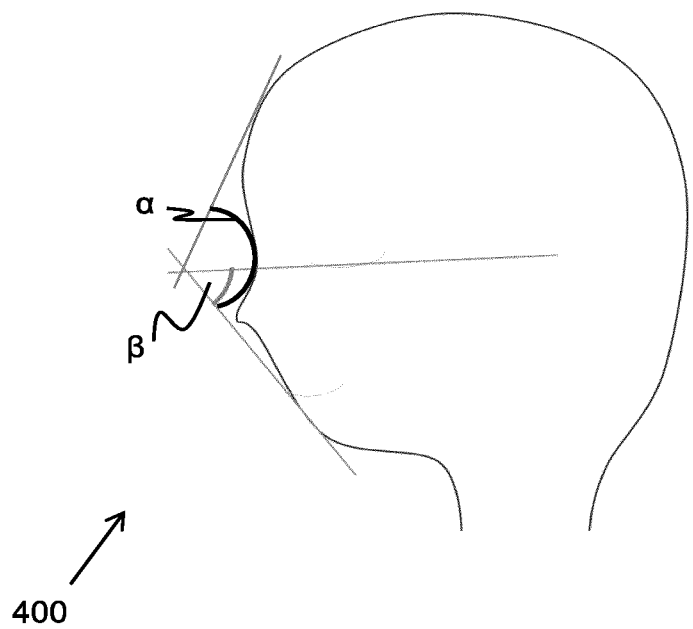
FIG. 4 shows a schematic mid-sagittal plane view of a fetus head.

FIG. 4 shows a mid-sagittal plane view 400 of a fetus.

From this view, it is possible to measure both a naso-mental angle, α, and an inferior facial angle, β. These angles may be measured manually by the user, or the angles may be automatically measured by way of the automatic placement of the measurement lines with respect to the profile.

The detection and identification of an anomalous feature may be triggered if one, or both, of the angle(s) is not within a normal predetermined range. For example, an angle below 142° for the naso-mental angle α may be considered anomalous according to "An objective measurement to diagnose micrognathia on prenatal ultrasound.", Palit, G. and Jacquemyn Y. and Kerremans M. *Clin Exp Obstet Gynecol* 35(2): 121-123, 2008. As a further example, an angles below 49.2° for the inferior-facial angle may be considered anomalous according to "The fetal mandible: a 2D and 3D sonographic approach to the diagnosis of retrognathia and micrognathia.", Rotten D., Levaillant J. M., Marthinez, H. Ducou le Pointe, H. and Vicaut, E. *Ultrasound Obstet Gynecol*, 19: 122-130 (2002).

Figure 5:
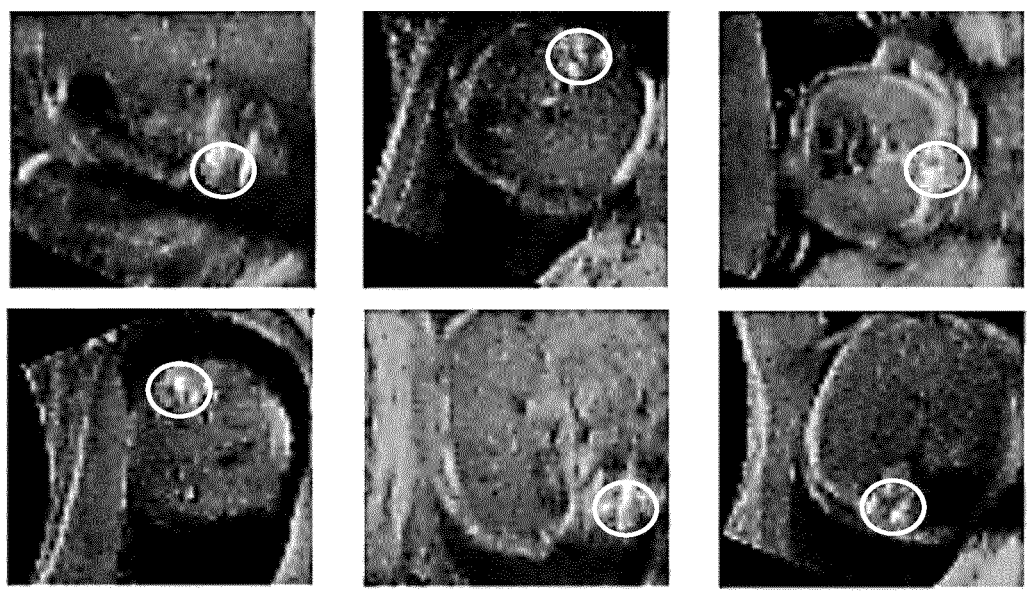
FIG. 5 shows example images of 2D view planes extracted orthogonally to the fetal spine.

FIG. 5 shows several images 500 of 2D views extracted orthogonally to the spine of a fetus.

The vertebrae have been highlighted by the white circles on the images for clarity. It is clear to see from these images that the fetal vertebrae are prominent features of the fetal ultrasound images that may be used as a reference structure for navigating a 3D ultrasound volume. In other words, the vertebra may be used as a structural feature for navigating the 3D ultrasound image volume along the anatomical reference structure of the spine.

Figure 6:
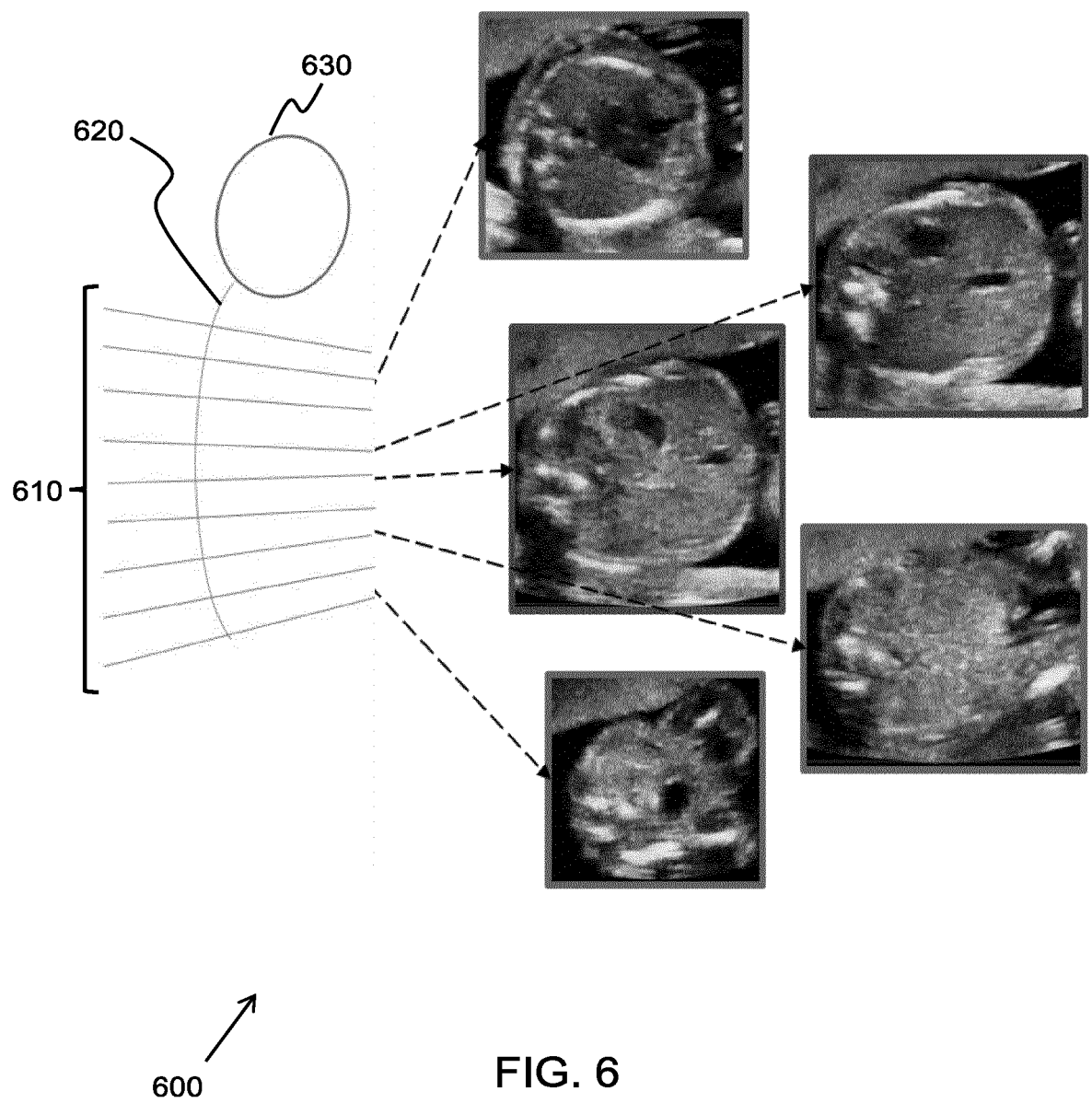
FIG. 6 shows fetal image slices in relation to the fetal spine.

FIG. 6 shows a schematic representation 600 of stack 610 of ultrasound images aligned using the fetal spine 620 as a reference.

A described above, the stack 610 of ultrasound images may be extracted starting at the fetal head 630 and progressing along the spine until the limit of the initially obtained 3D ultrasound image is reached. If the entire fetus is contained within the 3D ultrasound image volume, the stack of ultrasound images may contain a cardiac view and a renal view.

Further, the stack of ultrasound images may be extracted from a starting point other than the fetal head 630.

The examples described above have been explained in the context of fetal screening; however, it will be appreciated that the described methods may also be applied to any other medical ultrasound imaging process where the obtaining of complementary views may be required.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented ultrasound imaging method, the method comprising:
 obtaining a first ultrasound image comprising a first region of interest of a subject with an ultrasound probe of an ultrasound system;
 analyzing one or more features of the first ultrasound image;
 identifying an anomalous feature of the first region of interest based on the analysis of the one of more features;
 automatically generating a list of possible complementary ultrasound views of the subject, wherein the list of possible complementary ultrasound views of the subject are additional views of interest related to the identified anomalous feature, wherein the list of possible complementary ultrasound views is selected based on at least one of:
  the identified anomalous feature; or
  a condition correlated with the identified anomalous feature;
 obtaining one or more previously acquired ultrasound images stored in the ultrasound imaging system;
 automatically selecting a subset of the one or more previously acquired ultrasound images, wherein the subset of previously acquired ultrasound images corresponds to one or more possible complementary ultrasound views from the list; and displaying, on a display of the ultrasound imaging system, the subset of previously acquired ultrasound images to a user.

2. A method as claimed in claim 1, wherein the one or more previously acquired ultrasound images comprises a 3D ultrasound image.

3. A method as claimed in claim 2, wherein automatically selecting the subset of the one or more previously acquired ultrasound images further comprises:

extracting an anatomical reference structure; and obtaining a complementary 2D view group by extracting one or more 2D planes of interest from the 3D ultrasound image based on the extracted anatomical reference structure.

4. A method as claimed in claim 3, wherein automatically selecting the subset of the one or more previously acquired ultrasound images comprises:

extracting a structural feature from the anatomical reference structure;

determining whether the anatomical reference structure can be tracked in the 3D ultrasound image based on the structural feature; and extracting, in response to the anatomical reference structure being tracked in the 3D ultrasound image, 2D planes of interest from the 3D ultrasound image by using the anatomical reference structure as an anatomical landmark.

5. A method as claimed in claim 4, wherein the anatomical reference structure comprises one or more of:

an organ; or a skeletal structure.

6. A method as claimed in claim 5, wherein, when the anatomical reference structure comprises the organ, the organ comprises one or more of: a heart; a kidney; a bladder; or a stomach; and wherein, when the anatomical reference structure comprises the skeletal structure, the skeletal structure comprises one or more of: a skull; a vertebra; a ribcage; a femur; or a humerus.

7. A method as claimed in claim 1, wherein the identifying of the anomalous feature of the region of interest comprises performing organ detection.

8. A method as claimed in claim 1, wherein the region of interest comprises a part of a fetus.

9. A method as claimed in claim 8, wherein the identifying of the anomalous feature of the region of interest comprises performing skull and mid-sagittal brain plane detection on the fetus.

10. A method as claimed in claim 9, wherein the mid-sagittal brain plane detection comprises:

performing a multiresolution analysis; and performing Hough detection.

11. A method as claimed in claim 8, wherein the identifying of the anomalous feature of the region of interest comprises:

extracting a profile of the fetus; and obtaining, based on the profile of the fetus:

a naso-mental angle ($\alpha$); or an inferior facial angle ($\beta$).

12. The method of claim 1, wherein automatically generating the list of possible complementary ultrasound images views relates to the identified anomalous feature, and then the availability of listed complementary views is from the list of possible complementary ultrasound images views is determined based on previously acquired ultrasound images or the first ultrasound image.

13. The method of claim 1, wherein the list comprises at least one of:

complementary views of the first region; or complementary views of a second region.

14. The method of claim 1, wherein the list of possible complementary ultrasound views comprises at least one of cerebral views, facial rendering, genito-urinary tract views, cardiac views, and finger rendering.

15. The method of claim 1, wherein the automatically generating the list is only performed in response to an anomalous feature being identified.

* * * * *